US00PP35084P2

(12) United States Plant Patent
Hansen

(10) Patent No.: US PP35,084 P2
(45) Date of Patent: Apr. 4, 2023

(54) ***DIANTHUS* PLANT NAMED 'RED ROUGE'**

(50) Latin Name: ***Dianthus* hybrid**
Varietal Denomination: Red Rouge

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,682

(22) Filed: Oct. 13, 2022

(51) Int. Cl.
*A01H 5/02* (2018.01)
*A01H 6/30* (2018.01)

(52) U.S. Cl.
USPC ..... Plt./283
CPC ..... *A01H 6/305* (2018.05)

(58) Field of Classification Search
USPC ..... Plt./283
CPC ..... A01H 6/305; A01H 5/02
See application file for complete search history.

*Primary Examiner* — Keith O. Robinson

(57) ABSTRACT

A new and unique plant cultivar of perennial carnation or pinks, *Dianthus* plant named 'Red Rouge' with numerous, single, lightly-sweet fragrant flowers producing a full rounded face. Each flower has five overlapping petals that are burgundy red with irregularly rosy-pink flecking and edges. The flowering season is strong for four weeks beginning in late spring and continues less densely to early fall. The habit is compact and dense with glaucous blue-green foliage.

1 Drawing Sheet

Botanical denomination: *Dianthus* hybrid.
Cultivar designation: 'Red Rouge'.

STATEMENT REGARDING PRIOR DISCLOSURES UNDER 37 CFR 1.77(b)(6)

The first enabling disclosure as a sale of the new plant was on Oct. 22, 2021 by Green Leaf Plants® (a division of Aris Horticulture, Inc.) which obtained the new plant from Walters Gardens, Inc. Walters Gardens, Inc. also introduced the new plant on Feb. 1, 2022, in the form of photographs and a brief description on a website operated by Walters Gardens, Inc. followed on Jun. 8, 2022, as a photograph and brief description in the "Walters Gardens 2022-2023 Catalog." Walters Gardens, Inc. obtained the plant and all information relating thereto, from the inventor. No plants of *Dianthus* 'Red Rouge' have been sold, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of carnation or pinks from the genus *Dianthus* and given the cultivar name 'Red Rouge'. The new plant was the result of an intentional cross on Nov. 17, 2014 under the direction of the inventor between the proprietary, unreleased, unnamed hybrid known only by the breeder code 12-85-1 (not patented) as the female or seed parent and the male or pollen parent is the proprietary, unreleased, unnamed hybrid known only by the breeder code 12-47-4 (not patented). The cross was harvested and sown in the spring of 2015. The new hybrid was first selected from trials at a wholesale perennial nursery in Zeeland, Mich. during the summer of 2017 as a single seedling clone and given the breeder code number 14-40-1 later in the evaluation processes. *Dianthus* 'Red Rouge' has been asexually propagated at the same nursery in Zeeland, Mich. since 2019 using traditional shoot-tip cutting procedures and later sterile shoot-tip tissue culture and found to reproduce plants that are identical and exhibit all the characteristics of the original plant in successive generations.

SUMMARY OF THE INVENTION

*Dianthus* 'Red Rouge' has not been evaluated under all possible environmental conditions. The phenotype may vary with variations in environment conditions including: growing temperature, available sunlight, nutrients, water, etc. without a change in the genotype of the plant.

The closest comparison plants to the new plant known to the inventor include: 'Paint the Town Magenta' U.S. Plant Pat. No. 29,222, 'Paint the Town Fuchsia' U.S. Plant Pat. No. 28,636, KAHORI® 'Scarlet' (not patented), 'Paint the Town Red' U.S. Plant Pat. No. 33,293, 'Devon Xera' U.S. Plant Pat. No. 14,895 and 'Wp11 TYR04' U.S. Plant Pat. No. 25,077.

'Paint the Town Magenta' has a slightly smaller habit, the flowers are slightly smaller and of vibrant magenta-pink, and the petals do not have the darker red bar. 'Paint the Town Fuchsia' has a slightly smaller habit, but the flowers are smaller and fuchsia colored with lavender centers. KAHORI® 'Scarlet' has smaller habit with more light green foliage, the petals are narrower with less overlapping and solid scarlet colored without the darker center marking, and the flowers are less rounded. 'Paint the Town Red' has a slightly smaller habit, the flowers smaller are more reddish colored with a smaller dark eye. 'Devon Xera' has a slightly larger habit, flowers that are crimson-colored, and foliage that is more yellowish-green. 'Wp11 TYR04' has a very dark red center that bleeds into the margin of the flower petals.

The female parent, 12-85-1, had a pinkish flower with a dark red eye concentrated near the center. The male parent, 12-47-4, had a dark red without the dark red eye.

*Dianthus* 'Red Rouge' is distinct from its parents and all other *Dianthus* known to the applicant in the following combined traits:

1. Single large flowers with five overlapping petals forming a full rounded face;
2. Petals have moderately coarsely dentate apex;
3. Petal color is burgundy red with irregularly rosy-pink flecking and edges;
4. Numerous flowers per plant on heavily-branched upright stems;
5. Prolonged flowering period with a strong flush in late spring and continuing to early fall;
6. Compact habit and dense, glaucous, blue-green foliage.

BRIEF DESCRIPTION OF THE DRAWINGS

The photographs of 'Red Rouge' are of a two-year-old plant grown in full-sun trial garden in Zeeland, Mich. showing the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
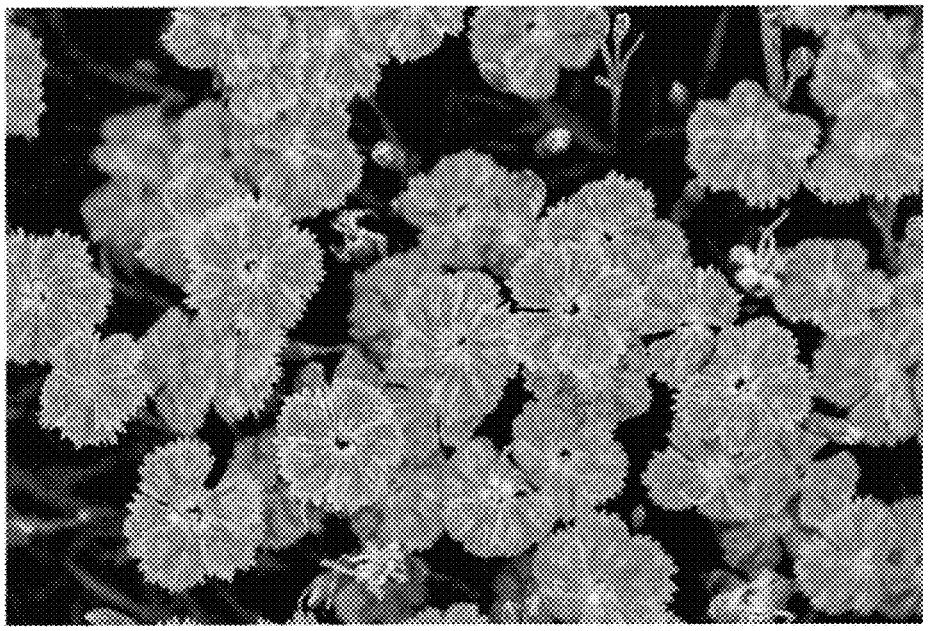
FIG. 1 shows the habit of the plant in mid-season flowering.
Figure 2:
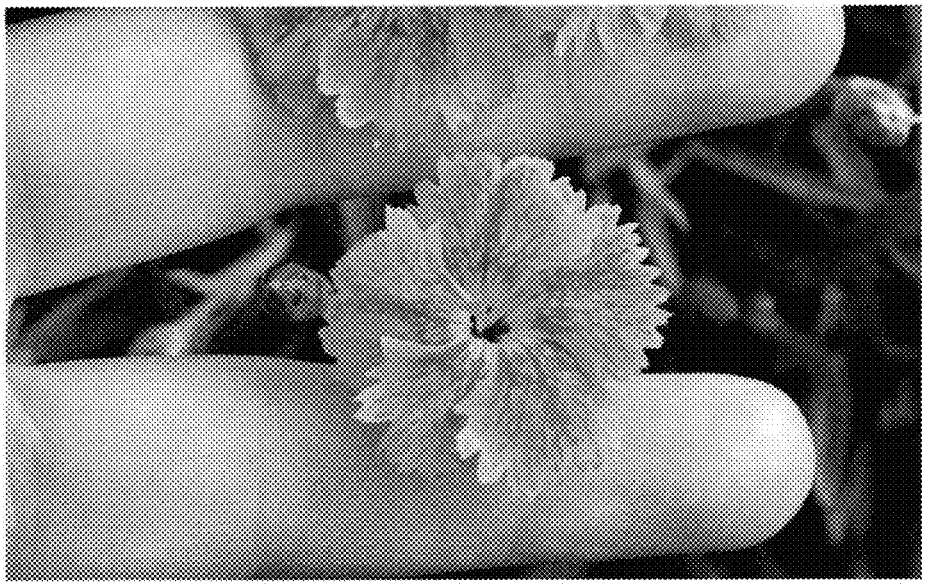
FIG. 2 shows a close-up of the flowers and buds.

The following detailed description of 'Red Rouge' is based on observations of two-year-old plants in a partially shaded greenhouse at a nursery in Zeeland, Mich. with supplemental watering, light additions of fertilizer and free of other plant growth regulators. All color usage is in accordance with the 2015 edition of The Royal Horticultural Colour Chart except where common dictionary terms are used.

Botanical classification: *Dianthus* hybrid;

Parentage: The female or seed parent is 12-85-1; the male or pollen parent is 12-47-4;

Plant habit: Caespitose, herbaceous, evergreen, winter-hardy perennial; stems and peduncles highly branched, mostly erect stems to slightly arching; height of foliage about 19 cm and about 47 cm across; height in flower is about 23 cm;

*Root system*.—Fine, fibrous; color nearest RHS 155D.

*Vigor*.—Good, spring planted plugs finish in 3.8-liter pots in seven to eight weeks.

Foliage:

*Leaf type*.—Simple, linear, opposite, decussate, sessile, glabrous, glaucous both adaxial and abaxial; margin entire to micro-serrulate; apex narrowly acute; base truncate, decurrent, clasping; straight; no fragrance detected; glaucosity medium.

*Leaf dimensions*.—To about 70 mm long and about 3.5 mm wide near middle, average about 60 cm long and 3 mm wide.

*Leaf color*.—Young expanding and mature leaves adaxial and abaxial blend between RHS N138B and RHS 189B.

*Venation*.—Not pronounced; obscurely pinnate, coloration same as that of leaf top and bottom.

Stems: About 100 per plant; upright; cylindrical, hollow; glabrous; glaucous; branching in upper and lower nodes;

*Stem size*.—About 20 cm long to peduncle and about 2 mm diameter at base.

*Stem color*.—Proximal portion nearest RHS N199B and distal portion nearest RHS 139A without glaucous bloom and with glaucous bloom between RHS 189B and RHS N138B.

*Branching*.—Numerous; typically alternate from lower nodes; about 4 per main stem and about 100 per plant in late spring peak; branch size average about 10 cm long and 1.5 mm diameter at time of initial flowering.

*Nodes*.—About 3 mm across; color between RHS 189B and RHS N138B.

*Internodes*.—About 10 to 14 per stem before peduncle; average about 1.3 cm apart depending on growing temperature, shorter in cooler conditions.

*Inflorescence*.—Flowering in the upper 8 cm and to about 5 cm across; with an average of two flowers per inflorescence.

*Flower bud*.—Slowly opening; glabrous; glaucous; with petals still tight but extending from calyx: cylindrical with attenuate base and rounded apex; about 19 mm long and 5 mm across; without extrusion of styles.

*Flower bud color*.—With petals extended beyond calyx petal portion nearer RHS 64A than RHS 64B; calyx between RHS 138A and RHS N138B and proximally, moderately to heavily tinted, concentrated, random, small areas nearest RHS N186C.

Flower:

*Type*.—On terminal, cymose inflorescence; perfect; salverform; actinomorphic; single.

*Attitude*.—Upright to slightly outwardly around perimeter of plant.

*Dimension*.—About 28 mm across and extending about 33 mm above base of calyx tube and 6 mm wide at apex of calyx.

*Flowers per stem*.—Up to 4, average 2.

*Pedicel*.—Glaucous, glabrous, cylindrical, stiff; upright.

*Pedicel size*.—Variable length from 2 mm to about 27 mm long and about 1.5 mm diameter.

*Pedicel color*.—Between RHS 138A and RHS N138B.

*Flower period*.—Late spring with a strong flush for about four weeks and continuing through early fall in Michigan.

*Flower fragrance*.—Lightly spicy.

*Flower lasting quality*.—Individually about seven to ten days on or cut from plant.

*Corolla profile*.—Distal 13 mm flat; proximal portion forming a lose tube in calyx.

*Petals*.—Five; glabrous adaxial and abaxial except at base of adaxial limb puberulent; consisting of a rounded limb and a claw; limb nearly semi-circular, and limb and claw combined are flabellate; limb apex and margin deeply dentate to bidentate with main teeth to about 2.5 mm long and 2 mm wide at base, and minor teeth to about 0.3 mm long and 0.2 mm wide; limb base attenuate toward claw; claw with attenuate base; bent outwardly at limb base creating a flat rounded face; persistent; having a darker eye, darker proximal center stripe, and darker variable flakes 0.5 mm to about 3 mm long and 0.5 mm across.

*Petal dimensions*.—Limb to about 15 mm long and 16 mm wide; claw about 17 mm long and 6 mm wide tapering to attenuate base of about 1.0 mm across; whole petal to about 32 mm long, to about 32 mm long; darker eye extending from near center to about two-thirds of the way to apex.

*Petal color*.—Young adaxial claw base nearest RHS 145D, claw distally nearest RHS 63B, limb distal and center flecking portions nearest RHS 54A, irregular center of 53A; young abaxial claw base nearest RHS 145D, distal claw nearest RHS 62C, limb between RHS 63B and RHS 63C; mature adaxial claw nearest RHS 145C, claw distally nearest RHS 62B, limb distal and center flecking portion between RHS 53B and RHS 53C, irregular center between RHS 63C and RHS 62B, with margin occasionally lightening to nearest RHS 69B; mature abaxial claw base nearest RHS 145D, distal claw nearest RHS 62C, limb between RHS 63B and RHS 63C.

*Calyx*.—Tubular; to about 19 mm long and 5 mm diameter at apex.

*Sepals*.—Five; acute apex and fused in basal 15 mm forming five-toothed calyx tube; glabrous adaxial and abaxial; glaucous abaxial, matte adaxial; margins entire to micro-ciliolate.

*Sepal size*.—Individually about 19 mm long and about 3 mm across at fusion.

*Sepal color*.—Adaxial nearest RHS 138C; abaxial nearest RHS 146B with apices strongly blushed to solid RHS N77C and base nearest RHS 138C.

*Peduncle*.—Glabrous; glaucous; hollow, cylindrical; stiff; about 8 cm long and about 2 mm diameter at base; attitude mostly upright to slightly arching.

*Peduncle color*.—Nearest RHS N138B with light glaucous bloom.

*Epicalyx*.—Two pairs subtending each flower; both pairs adpressed; opposite, glaucous, glabrous; sessile, margin entire; ovate; inner pair narrowly acute apex and truncate base, to about 8 mm long and about 6 mm across near middle; outer pair with very short narrowly acute apex, truncate clasping base, to about 9 mm long and about 3 mm wide.

*Epicalyx color*.—Both pairs variable; adaxial center nearest RHS 147B, abaxial center nearest RHS N138A, adaxial and abaxial margins variable nearest RHS 150D and between RHS 146D and RHS 145C; with heavy anthocyanin pigment of nearest RHS N186B concentrated in variable shaped spots near apex.

*Androecium*.—Not observed.

*Gynoecium*.—Single; to about 29 mm long; Style: bifurcate just above ovary; shoulder absent; to 21 mm long and 1 mm across; color proximally nearest RHS NN155D, distally between RHS 63B and RHS 61B, middle portion between RHS 61C and RHS 63C; Stigma: slightly flattened abaxial to adaxial; puberulent along adaxial surface; about 1 mm long and 1 mm wide; color nearest RHS 61B; Ovary: superior; cylindrical; acute apex and truncate base; smooth, lustrous; about 8 mm long and 4.0 mm diameter; color distally nearest RHS 145A and proximally nearest RHS 150C.

Fruit: Capsule; ovoid; about 9 mm long and 4 mm diameter; truncate apex and attenuate base; glabrous; releasing seed by four apical valves; color at maturity between RHS 199D and RHS 164D;

Seed: Slightly flattened ovoid; about 1 mm long and 0.5 mm across; about 30 per fruit; color nearest RHS 203B;

Disease resistance: The new plant is resistance to center die out from fungus or high temperatures.

Growth: The plant grows best with adequate moisture and well-drained soil but is able to tolerate some drought once established. Hardiness at least from USDA zone 4 through zone 9.

It is claimed:

1. A new and distinct *Dianthus* plant named 'Red Rouge' essentially as herein described and illustrated.

* * * * *